(12) United States Patent
Ogle

(10) Patent No.: US 9,539,413 B2
(45) Date of Patent: Jan. 10, 2017

(54) CATHETER HANDLE

(75) Inventor: David Ogle, Cowan (AU)

(73) Assignee: CathRx Ltd, Homebush Bay (AU)

( * ) Notice: Subject to any disclaimer, the term of this patent is extended or adjusted under 35 U.S.C. 154(b) by 186 days.

(21) Appl. No.: 13/697,299

(22) PCT Filed: May 10, 2011

(86) PCT No.: PCT/AU2011/000529
§ 371 (c)(1),
(2), (4) Date: Nov. 9, 2012

(87) PCT Pub. No.: WO2011/140583
PCT Pub. Date: Nov. 17, 2011

(65) Prior Publication Data
US 2013/0060236 A1 Mar. 7, 2013

Related U.S. Application Data

(60) Provisional application No. 61/333,576, filed on May 11, 2010.

(51) Int. Cl.
*A61M 25/08* (2006.01)
*A61M 25/01* (2006.01)
(Continued)

(52) U.S. Cl.
CPC ............ *A61M 25/0136* (2013.01); *A61B 5/04* (2013.01); *A61B 5/0422* (2013.01); *A61B 5/6856* (2013.01);
(Continued)

(58) Field of Classification Search
CPC ............ A61M 25/01; A61M 25/0102; A61M 25/0105; A61M 25/0133; A61M 25/0136; A61M 25/0152; A61M 2025/0161; A61M 2025/0098; A61M 2025/0163; A61M 25/0147; A61B 18/148; A61B 2018/1407; A61B 5/6856; A61B 5/6857
(Continued)

(56) References Cited

U.S. PATENT DOCUMENTS 5,327,905 A * 7/1994 Avitall ..................... 600/585
5,383,923 A * 1/1995 Webster, Jr. ............. 607/125
(Continued)

FOREIGN PATENT DOCUMENTS

CA 2138236 5/1996
EP 0904797 A2 3/1999
(Continued)

OTHER PUBLICATIONS

PCT International Search Report, International Application No. PCT/AU2011000529, mailed Sep. 8, 2011, four (4) pages.
(Continued)

*Primary Examiner* — Quynh-Nhu H Vu
(74) *Attorney, Agent, or Firm* — TraskBritt

(57) ABSTRACT

A catheter handle includes a handle body having a proximal end and a distal end and a passage extending between the proximal end and the distal end. The handle body comprises a plurality of shell parts that can be separated to access an interior of the handle body. The handle body further includes a connector mounted at the proximal end of the handle body and a strain relief arranged at the distal end, the strain relief and the connector being removably arranged relative to the handle body.

20 Claims, 11 Drawing Sheets

(51) Int. Cl.
    *A61B 5/04*         (2006.01)
    *A61B 5/042*      (2006.01)
    *A61B 5/00*         (2006.01)
    *A61B 18/14*      (2006.01)
    *A61M 25/00*     (2006.01)

(52) U.S. Cl.
    CPC ...... *A61B 18/148* (2013.01); *A61B 2018/1407* (2013.01); *A61M 25/0147* (2013.01); *A61M 25/0152* (2013.01); *A61M 2025/0098* (2013.01); *A61M 2025/0161* (2013.01); *A61M 2025/0163* (2013.01)

(58) Field of Classification Search
    USPC .................. 604/95.01, 95.04–95.05; 606/129
    See application file for complete search history.

(56) References Cited

U.S. PATENT DOCUMENTS

| | | | | |
|---|---|---|---|---|
| 5,545,200 | A | * | 8/1996 | West et al. ................. 607/122 |
| 5,611,777 | A | * | 3/1997 | Bowden et al. ........... 604/95.01 |
| 5,643,255 | A | * | 7/1997 | Organ ................ A61B 18/1492 606/34 |
| 5,656,030 | A | * | 8/1997 | Hunjan ............. A61M 25/0147 604/264 |
| 5,662,606 | A | | 9/1997 | Cimino et al. |
| 5,666,970 | A | * | 9/1997 | Smith ................ A61M 25/0136 600/585 |
| 5,741,320 | A | * | 4/1998 | Thornton .......... A61M 25/0136 604/95.01 |
| 5,779,669 | A | * | 7/1998 | Haissaguerre et al. .... 604/95.01 |
| 5,792,104 | A | | 8/1998 | Speckman et al. |
| 5,910,129 | A | | 6/1999 | Koblish et al. |
| 5,987,344 | A | | 11/1999 | West et al. |
| 6,013,052 | A | * | 1/2000 | Durman et al. .......... 604/95.01 |
| 6,263,224 | B1 | * | 7/2001 | West ............................. 600/373 |
| 6,542,781 | B1 | | 4/2003 | Koblish et al. |
| 6,554,794 | B1 | * | 4/2003 | Mueller ............ A61B 17/3478 604/528 |
| 6,805,675 | B1 | * | 10/2004 | Gardeski ........... A61M 25/0136 600/585 |
| 6,913,594 | B2 | * | 7/2005 | Coleman ........... A61M 25/0136 600/585 |
| 2002/0072712 | A1 | | 6/2002 | Nool et al. |
| 2002/0165484 | A1 | | 11/2002 | Bowe et al. |
| 2003/0171723 | A1 | | 9/2003 | Ponzi |
| 2006/0264819 | A1 | | 11/2006 | Fischer et al. |
| 2007/0225641 | A1 | | 9/2007 | Schneider et al. |
| 2009/0024084 | A1 | | 1/2009 | Khosla et al. |
| 2009/0299282 | A1 | | 12/2009 | Lau et al. |
| 2013/0053876 | A1 | * | 2/2013 | Ogle ............................. 606/170 |
| 2013/0060236 | A1 | | 3/2013 | Ogle |
| 2013/0060237 | A1 | * | 3/2013 | Ogle ............................. 604/528 |

FOREIGN PATENT DOCUMENTS

| | | |
|---|---|---|
| EP | 1323448 A2 | 7/2003 |
| EP | 1676595 A1 | 5/2006 |
| EP | 2116272 A1 | 11/2009 |
| WO | 9634653 | 11/1996 |
| WO | 9637252 | 11/1996 |
| WO | 2006092014 A1 | 9/2006 |
| WO | WO2006135988 A1 | 12/2006 |
| WO | 2007038539 | 4/2007 |
| WO | WO2007089676 A1 | 8/2007 |
| WO | 2007128065 A1 | 11/2007 |
| WO | 2009114908 A1 | 9/2009 |
| WO | 2009142120 A1 | 11/2009 |

OTHER PUBLICATIONS

Supplemental European Search Report for Application No. EP 11 779 961.9, dated Oct. 15, 2013, 6 pages.
Written Opinion of the International Search Authority for International Application No. PCT/AU2011000529, dated Sep. 7, 2011, 8 pages.
International Preliminary Report on Patentability, for International Application No. PCT/AU2011000529, dated Nov. 13, 2102, 9 pages.

* cited by examiner

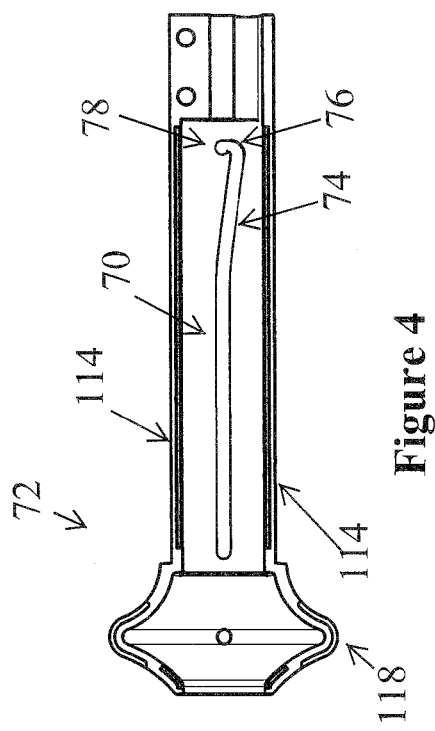
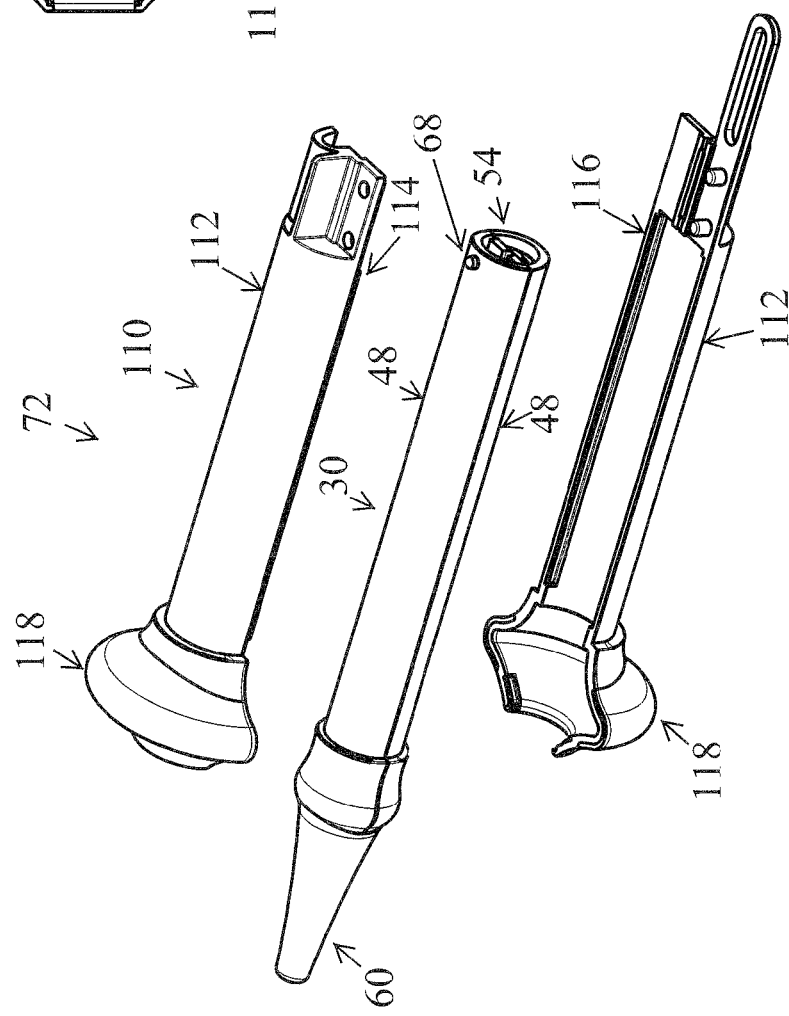
Figure 4
Figure 5

CATHETER HANDLE

CROSS-REFERENCE TO RELATED APPLICATIONS

This application is a national phase entry under 35 U.S.C. §371 of International Patent Application PCT/AU2011/000529, filed May 10, 2011, designating the United States of America and published in English as International Patent Publication WO 2011/140583 A1 on Nov. 17, 2011, which claims the benefit under Article 8 of the Patent Cooperation Treaty and under 35 U.S.C. §119(e) to U.S. Provisional Patent Application Ser. No. 61/333,576, filed May 11, 2010, the disclosure of each of which is hereby incorporated herein by this reference in its entirety.

TECHNICAL FIELD

This disclosure relates generally to a catheter and, more particularly, to a catheter shape adjustment mechanism and to a catheter including such shape adjustment mechanism.

BACKGROUND

Any discussion of the prior art throughout the specification should in no way be considered as an admission that such prior art is widely known or forms part of common general knowledge in the field.

Catheters are commonly used in medical practice to examine and treat the heart. They may be inserted into the cardiovascular system of the patient through small punctures in the skin. They may then extend through a vein into the heart where they sense the electrical activity of the heart. Some catheters may be able to treat the heart by ablating certain areas of the heart in the case of certain types of aberrant electrical activity. Catheters typically include a tubular structure such as a plastic tube with one or more electrodes attached to the tip of the tube, a deflection mechanism for guiding the tubular structure, and a control handle.

During their use in medical procedures, catheters are exposed to biological fluids in the human body. Because catheters come in contact with these bodily fluids, they are commonly designed to be single-use devices to avoid the transfer of viruses or bacteria from one patient to another. Disposing of the catheters after each procedure leads to significant expenses to the patient and the healthcare system, as well as creates a substantial amount of medical waste. Catheters, particularly the handles and sheaths of catheters, are typically an expensive piece of equipment. Catheter handles, in particular, often include proprietary electronics and other expensive components for increased functionality. These valuable components are lost when the device is disposed after a single use. Because catheters and catheter handles are expensive and their use produces a large amount of waste, certain institutions resterilize and reprocess catheters for re-use. Reprocessing single-use devices reduces the cost of a procedure and minimizes the medical waste generated.

Catheters, and catheter handles in particular, are typically fabricated as substantially integral devices where most components are joined together using permanent connections and seals. These types of catheter handles are difficult or impossible to resterilize reliably, and small particles of biological matter may be trapped within the catheter even after the sterilization process. In addition, because most components are permanently joined together, these components are lost when the catheter is disposed of after use, even if they were still fully functional.

DISCLOSURE

It is an object of the present invention to overcome or ameliorate at least one of the disadvantages of the prior art, or to provide a useful alternative.

An embodiment of the invention provides a catheter handle that includes a handle body having a proximal end and a distal end and a passage extending between the proximal end and the distal end, the handle body comprising a plurality of shell parts that can be at least partially separated from each other to access an interior of the handle body, a connector mounted at the proximal end of the handle body and a strain relief arranged distally of the handle body, the strain relief and the connector being removably arranged relative to the handle body.

The catheter handle may include a catheter sheath carrier received in the passage of the handle body, the strain relief being mounted on a distal end of the catheter sheath carrier. The catheter sheath carrier may be slidably received in the passage of the handle body to be slidably displaceable relative to the handle body between a first, retracted position relative to the handle body and a second, extended position relative to the handle body. The catheter sheath carrier may further comprise a sleeve defining a bore, and a support member for supporting a proximal part of a catheter sheath being received in the bore of the sleeve. The sleeve may comprise a plurality of parts that are able to be at least partially separated from each other to enable access to be gained to an interior of the sleeve.

The catheter sheath carrier and the catheter handle preferably include complementary guide formations for guiding displacement of the catheter sheath carrier relative to the handle body. The complementary guide formations may include a locking arrangement for locking the carrier at least in its first position relative to the handle body.

In an embodiment, the catheter handle further includes a steering control mechanism. The steering control mechanism may be axially displaceable relative to the handle body for effecting steering of a stylet of the catheter during use. The steering control mechanism preferably comprises a hollow, cylindrical element in which the catheter sheath carrier is received. The catheter handle may further include an adjustment device for adjusting the friction of displacement of the steering control mechanism relative to the handle body. The cylindrical element may comprise a plurality of parts that can be at least partially separated from each other to facilitate access to an interior of the cylindrical element. In addition, the steering control mechanism may include a seat for a component of a multi-component stylet.

In an embodiment, the catheter handle may further include a size adjuster for adjusting the size of a pre-formed shape at a distal end of a stylet attached to the handle body during use. The size adjuster may comprise a stylet carrier slidably displaceably arranged in the handle body and a collar mounted on an exterior of the handle body to be rotatable about a longitudinal axis of the handle body. The collar and the stylet carrier may have complementary motion conversion formations for converting rotary motion of the collar into a predefined motion of the stylet carrier. The stylet carrier may include a mounting formation for mounting a first component of the stylet. In addition, the handle body may define a seat for receiving a second component of the stylet during use.

Another embodiment of the invention provides a method of producing a catheter handle as described above.

According to another embodiment, there is provided a catheter including a catheter handle having a handle body having a proximal end and a distal end and a passage extending between the proximal end and the distal end, the handle body comprising a plurality of shell parts that can be at least partially separated from each other to access an interior of the handle body, a connector mounted at the proximal end of the handle body, and a strain relief arranged distally of the body, the strain relief and the connector being removably arranged relative to the handle body. The catheter further includes a multi-component stylet having a proximal end mounted in the passage of the handle body, the stylet having a distal part pre-formed into a predetermined shape, and a catheter sheath projecting distally through the strain relief, the catheter sheath defining a lumen in which the stylet is received so that the shape of the pre-formed distal part of the stylet is imparted to a distal part of the catheter sheath.

BRIEF DESCRIPTION OF THE DRAWINGS

Preferred embodiments of the invention will now be described, by way of example only, with reference to the accompanying drawings in which:

FIG. 4 shows a cross-sectional bottom view of a part of a steering control mechanism of the catheter handle carrying a component of the shape adjustment mechanism;

FIG. 5 shows a three-dimensional, exploded view of the steering control mechanism and shape adjustment mechanism of the catheter;

DETAILED DESCRIPTION

Figure 1:
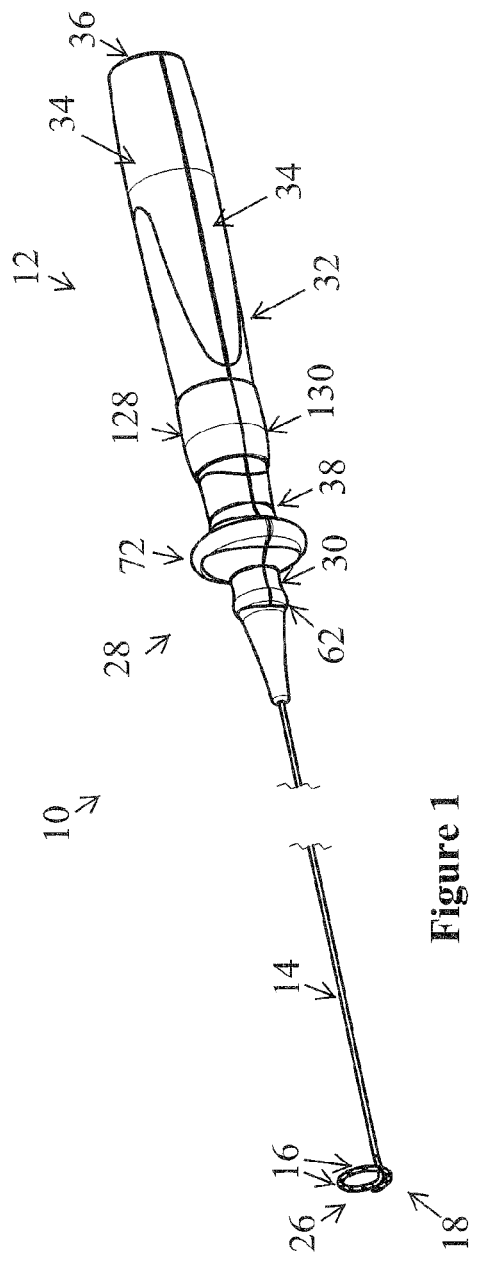
FIG. 1 shows a three-dimensional view of a catheter with a shape adjustment mechanism in an inoperative position.

In the drawings, reference numeral 10 generally designates an embodiment of a catheter. The catheter 10 comprises a catheter handle 12 from which a catheter sheath or electrode sheath 14 projects. The catheter sheath 14 carries a plurality of electrodes 16 at a distal part 18 of the catheter sheath 14. The electrodes 16 are used for diagnostic and/or therapeutic purposes.

The catheter further includes a stylet 20 (FIGS. 9 and 11-13). A proximal part 22 of the stylet 20 is received within the catheter handle 12 as will be described in greater detail below. The catheter sheath 14 has a lumen (not shown) in which the stylet 20 is received. As shown more clearly in FIG. 12, a distal part 24 of the stylet 20 is pre-formed into a shape, more particularly a loop shape 26. However, it will be appreciated that the distal part 24 of the stylet 20 could be pre-formed into any other desired shape such as, for example, a helix, a tapering helix, a pig tail shape, or any other desired shape.

The stylet 20 fits within the lumen of the catheter sheath 14 and the loop shape 26 of the distal part 24 of the stylet 20 is imparted to the distal part 18 of the catheter sheath 14 as shown in FIG. 1. For ease of explanation, the disclosure will be described with reference to the shape at the distal part 24 of the stylet 20 being the loop shape. However, it will be appreciated that what follows could be applicable to any other stylet 20 having a shaped distal part 24.

In an embodiment, the catheter 10 includes a shape release mechanism 28. The shape release mechanism 28 comprises the catheter handle 12 and an elongate catheter sheath carrier in the form of a sleeve 30 that is slidably received in the handle 12 to protrude distally from the handle 12.

The handle 12 comprises a handle body 32. The handle body 32 is made up of a plurality of shell parts 34, shown most clearly in FIG. 8. In the illustrated embodiment, the handle body 32 comprises two shell parts 34 that are substantially mirror images of each other. The handle body 32 has a proximal end 36 and a distal end 38. A passage 40 (FIG. 8) extends between the proximal end 36 and the distal end 38 of the handle body 32.

Figure 8:
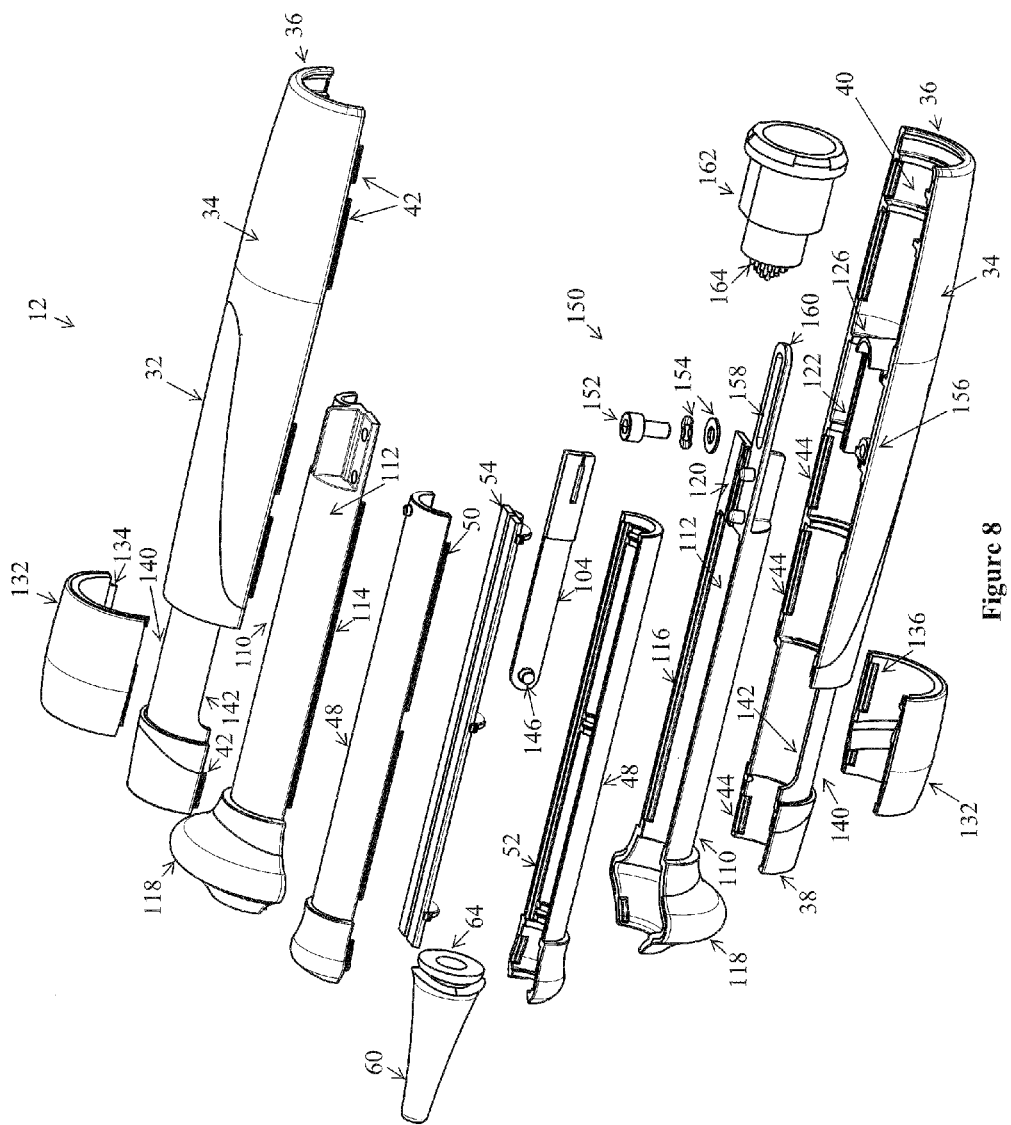
FIG. 8 shows a three-dimensional, exploded view of a handle of the catheter.

In the embodiment illustrated in FIG. 8, the two shell parts 34 are secured together by clips 42, carried on one of the shell parts 34, which are received in complementary receiving formations 44 in the other shell parts 34.

Figure 14:
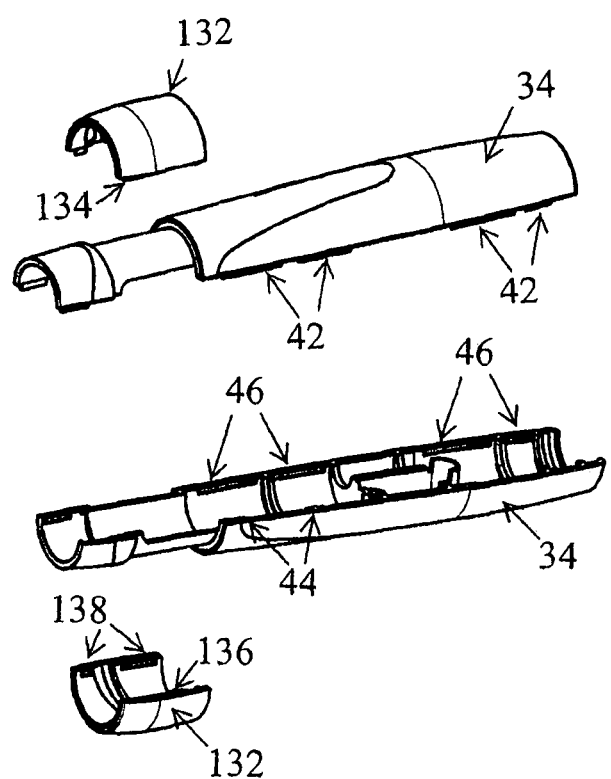
FIG. 14 shows a three-dimensional, exploded view of another embodiment of the handle of the catheter.

In the embodiment shown in FIG. 14, only one side of each shell part 34 has the clips 42 or receiving formations 44, as the case may be. The other side of the shell parts 34 of the handle body 32 are hinged together with wings 46 of the hinges shown in FIG. 14.

Regardless of the manner in which the shell parts 34 connect together, it is a simple process to open the handle body 32 by disengaging the shell parts 34 to enable access to be gained to an interior of the handle body 32. Further, it will be appreciated that, instead of clips, the shell parts 34 could be held together in other ways, for example, by being screwed together, by means of one or more spring clips received about the handle body 32, or the like.

Figure 3:
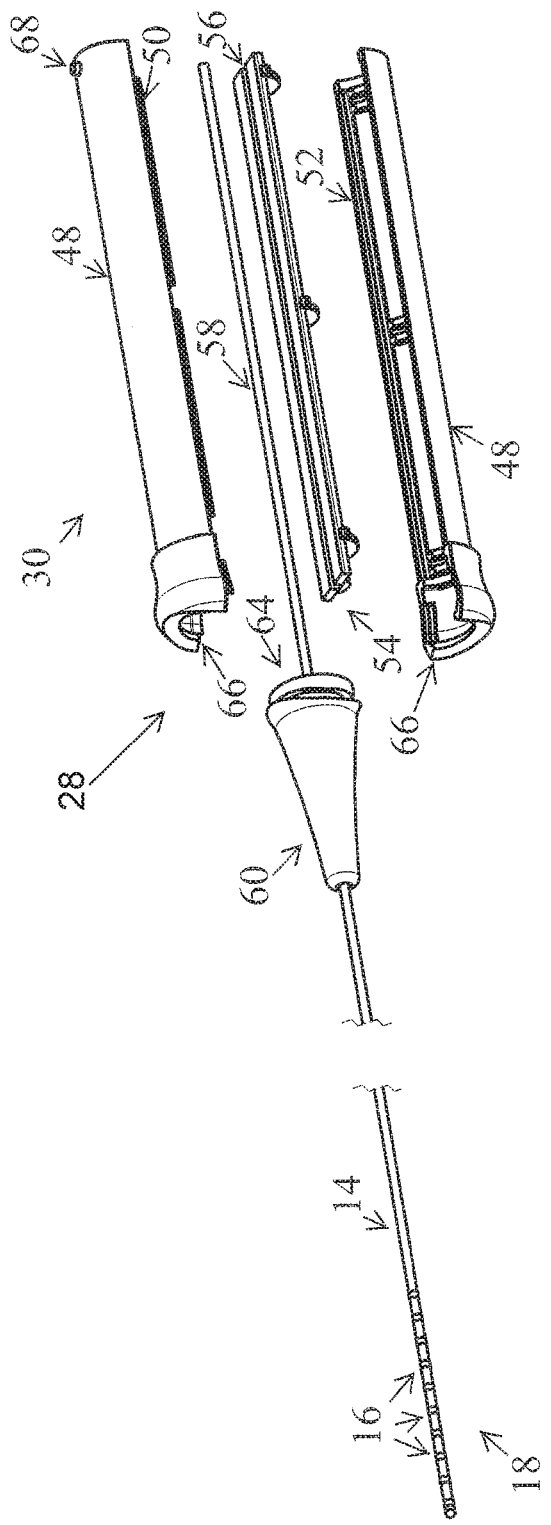
FIG. 3 shows a three-dimensional, exploded view of the shape adjustment mechanism of the catheter.
Figure 6:
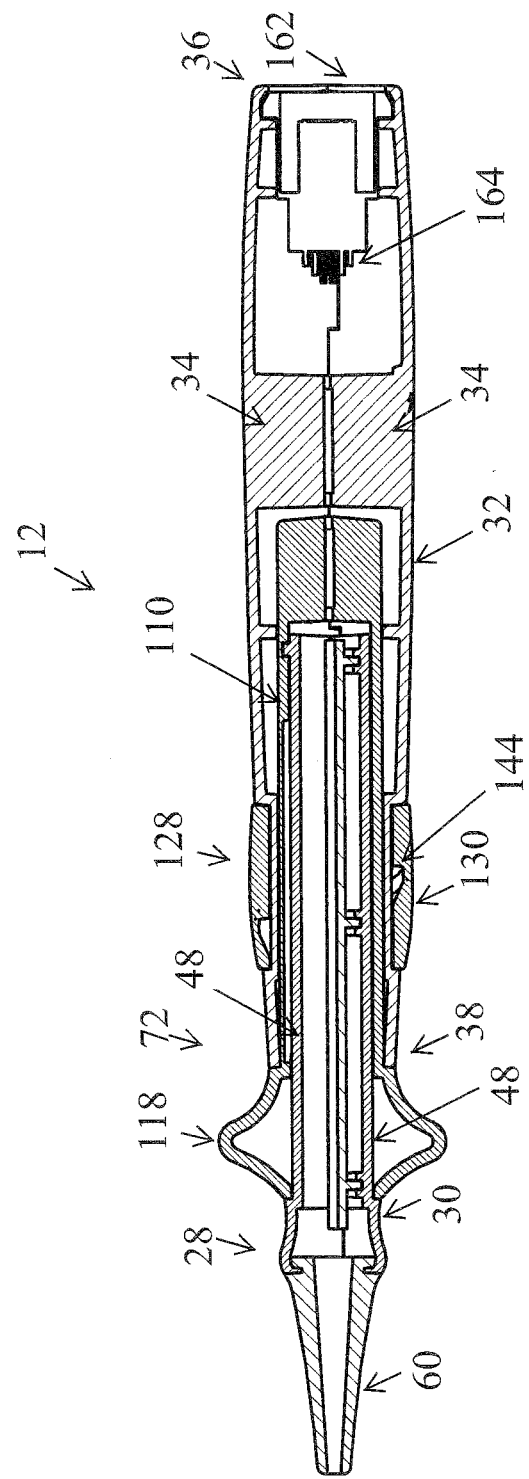
FIG. 6 shows a cross-sectional side view of a handle of the catheter with the shape adjustment mechanism in its inoperative position.
Figure 7:
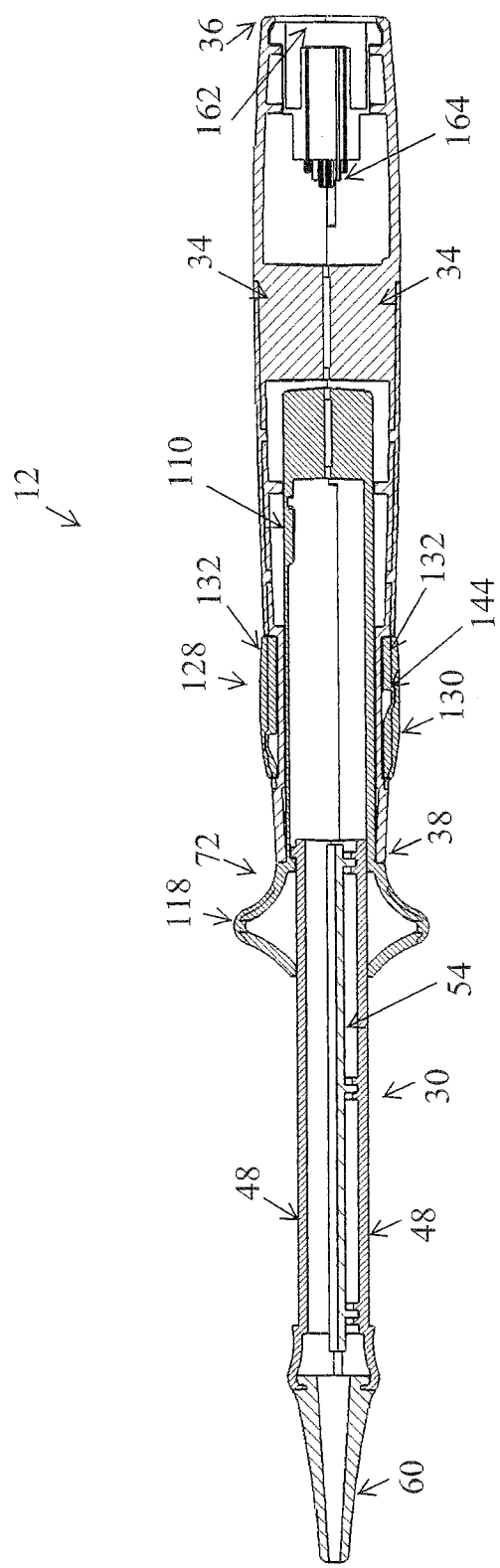
FIG. 7 shows a cross-sectional side view of a handle of the catheter with the shape adjustment mechanism in its operative position.

With reference to FIG. 3, the sleeve 30 of the shape release mechanism 28 comprises two parts 48. In the illustrated embodiment, the two parts 48 clip together via clips 50 and locating formations 52. As described above with reference to the shell parts 34 of the handle body 32, it will be appreciated that these parts 48 could also be hinged together and clipped or screwed together to form the sleeve 30.

The sleeve 30 surrounds a support member 54. The support member 54 has a longitudinally extending channel 56 formed in it. A proximal part 58 of the catheter sheath 14 is supported in the channel 56 of the support member 54. If desired, the proximal part 58 can be bonded in the channel 56 by means of a suitable adhesive.

The shape release mechanism 28 also includes a strain relief 60. The strain relief 60 is secured to a distal end 62 (FIGS. 1 and 2) of the sleeve 30. The strain relief 60 is of a resiliently flexible material and has a proximal collar 64 that engages a shoulder 66 on the parts 48 of the sleeve 30 to hold the strain relief 60 captive when the parts 48 of the sleeve 30 are secured together. The strain relief 60, being of a resiliently flexible material, also inhibits ingress of foreign matter, such as bodily fluid, into the interior of the sleeve 30 and, therefore, the interior of the catheter handle 12.

The shape release mechanism 28 includes complementary guide formations for guiding sliding displacement of the sleeve 30 relative to the handle body 32. The complementary guide formations comprise a pin 68 arranged at a proximal end of one of the parts 48 of the sleeve 30. A guide plate 70 (FIG. 4) is secured to a part of the catheter handle 12, more particularly, a steering mechanism 72 of the catheter handle 12. The steering control mechanism 72 will be described in greater detail below.

Figure 2:
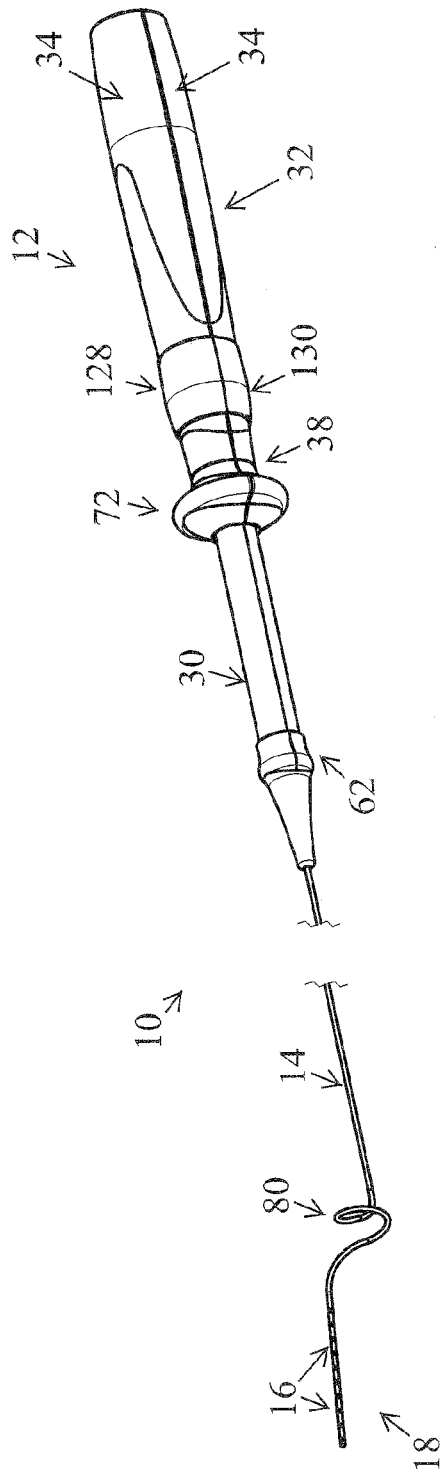
FIG. 2 shows a three-dimensional view of the catheter with the shape adjustment mechanism in an operative position.

The guide plate 70 defines a guide slot 74 that extends axially in the guide plate 70. The guide slot 74 is cranked and a locking arrangement in the form of a detent 76 is defined at a proximal end of the guide slot 74. Thus, when the sleeve 30 is in its retracted position as shown in FIG. 1, the pin 68 is received in the detent 76 at an extremity 78. To release the sleeve 30 to enable it to slide axially to the position as shown in FIG. 2, the sleeve 30 needs to be rotated so that the pin 68 moves away from the extremity 78 into alignment with the remainder of the guide slot 74. The sleeve 30 is then free to be extended to the position as shown in FIG. 2.

The purpose of the shape release mechanism 28 is to release the loop shape 26 when is snags on tissue in the patient's body during use. This can lead to complications and difficulty. As shown, the loop shape 26 is a tightly wound formation. However, by extending the catheter sheath 14 relative to the stylet 20 from the position shown in FIG. 1 to the position shown in FIG. 2, by extending the sleeve 30 relative to the handle 12, the distal part 24 of the stylet 20 is withdrawn from the distal part 18 of the catheter sheath 14 and adopts a position proximal the distal part 18 of the catheter sheath 14 as shown at 80 in FIG. 2. When the distal part 24 of the stylet 20 is withdrawn proximally relative to the distal part 18 of the catheter sheath 14, the tension in the distal part 24 of the stylet 20 is reduced causing the distal part 18 to adopt a more drawn out, less tightly wound shape and facilitates disentanglement or release of the shaped part of the catheter sheath 14 from tissue in which it may have become entangled.

As described above, the catheter handle 12 includes a steering control mechanism 72. This steering control mechanism 72 is used for steering the distal part of the catheter sheath 18 through the patient's vasculature and, also, for effecting deflection of the loop formation 26 at the distal part of the catheter sheath 14.

Figure 9:
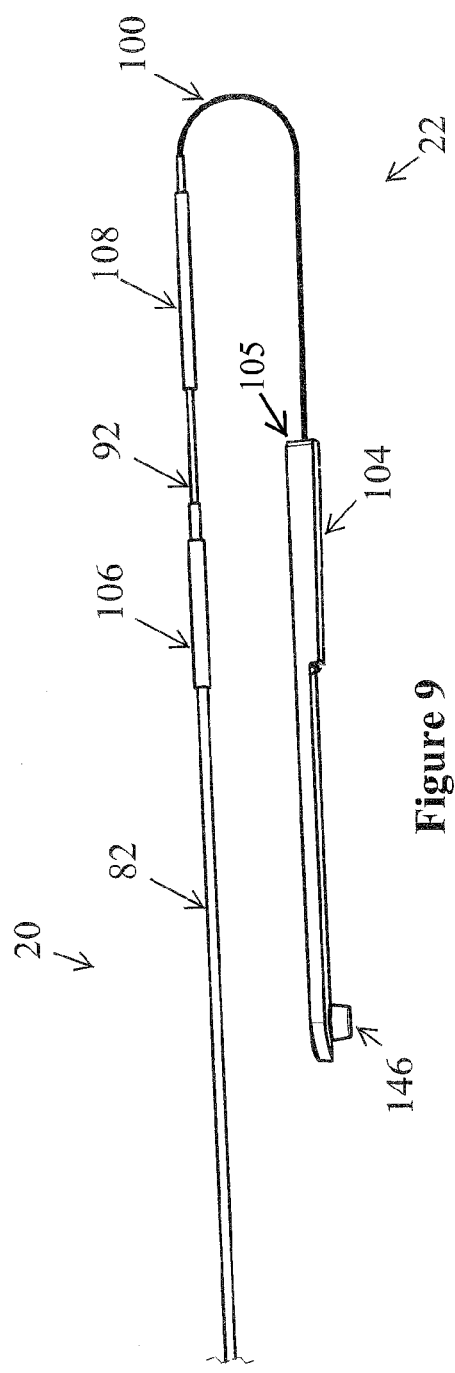
FIG. 9 shows a plan view of a proximal part of a stylet of the catheter.
Figure 11:
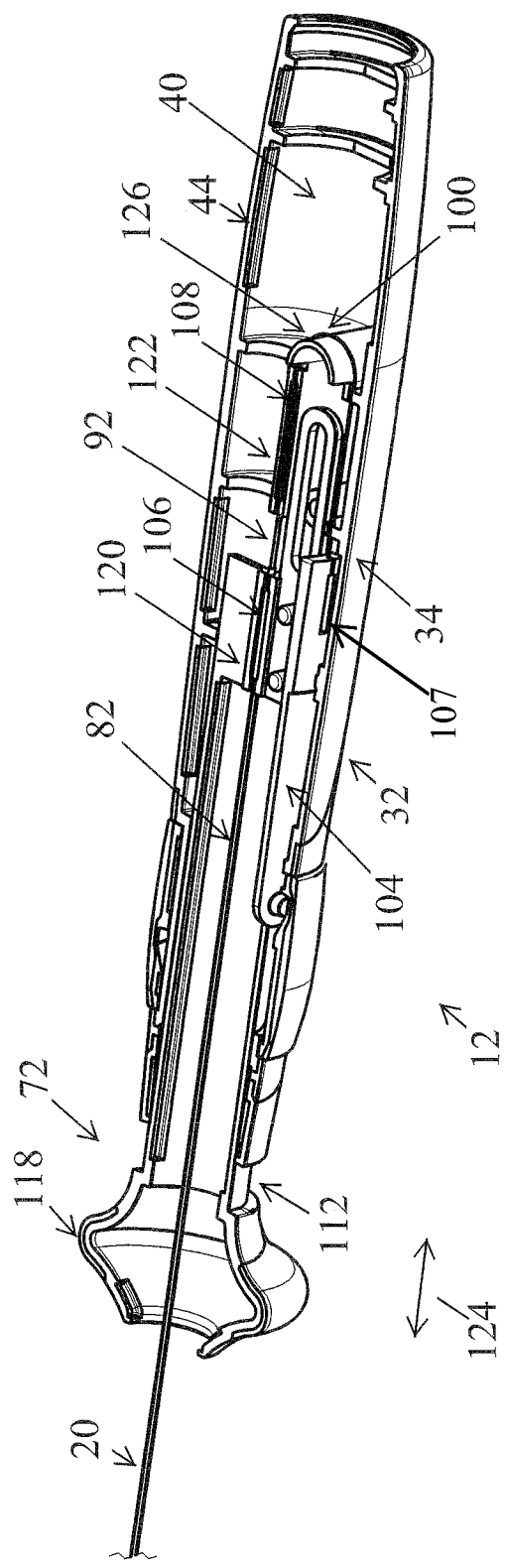
FIG. 11 shows a three-dimensional view of a part of the handle of the catheter showing the interrelationship between the proximal part of the stylet and the shape adjustment mechanism.
Figure 12:
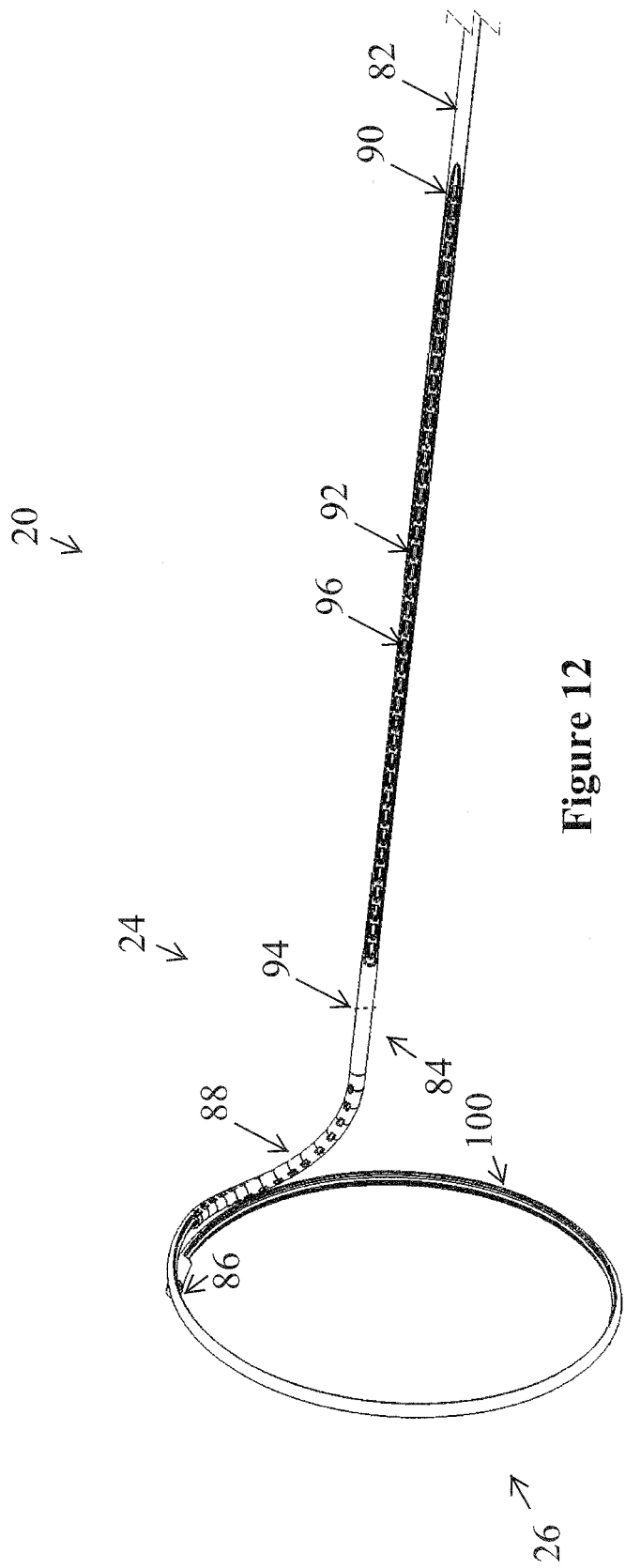
FIG. 12 shows a three-dimensional view of a distal part of the stylet.

Before describing the steering control mechanism 72 in greater detail, the stylet 20 will also be described to understand the operation of the stylet 20 of the catheter 10. FIG. 9 shows a proximal part of the stylet 20, FIG. 11 shows the proximal part of the stylet mounted in one of the shell parts 34 of the handle body 32 of the catheter handle 12, FIG. 12 shows a distal part of the stylet 20 and FIG. 13 shows a distal part of a component of the stylet 20 in the form of an outer tubular member 82.

Figure 13:
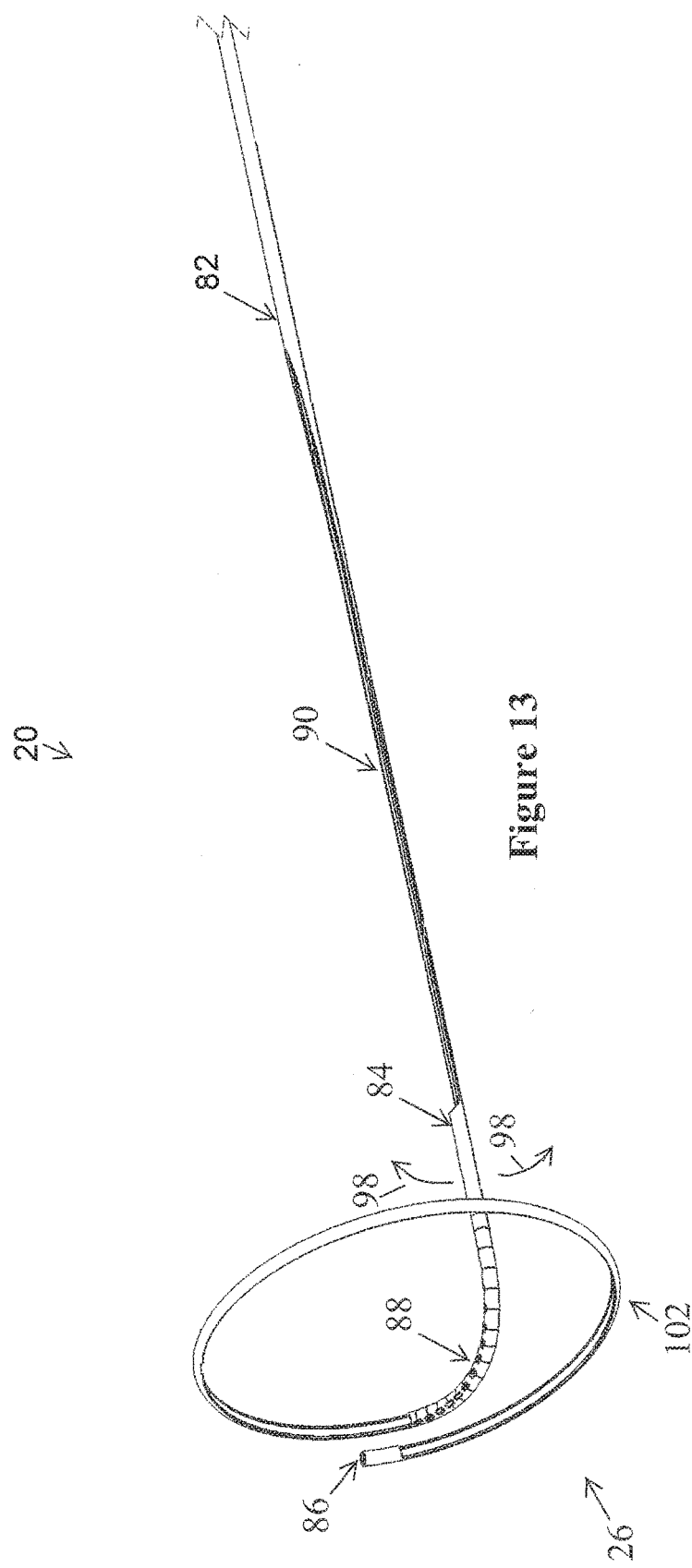
FIG. 13 shows a three-dimensional view of a distal part of an outer tube of the stylet.

The outer tubular member 82 has a distal part 84, which is shown in greater detail in FIG. 13. The distal part 84 of the outer tubular member 82 is pre-formed into the loop-shape 26 and has a distal end 86. The distal part 84 is cranked as shown at 88 so that the loop shape 26 lies in a plane transverse to a longitudinal axis of the outer tubular member 82. An elongate, cutaway, bend-enhancing portion 90 is formed in the distal part 84 of the tubular member 82 proximal to the cranked region 88. The portion 90 is a scalloped portion and has varying amounts cut away, increasing from the proximal end to the distal end of the cutaway portion 90 to facilitate deflection of the distal end of the loop shape 26 of the stylet 20 as will be described in greater detail below.

The stylet 20 includes an inner, tubular actuator 92. The actuator 92 has a distal end secured at 94 to the distal part 84 of the outer tubular member 82 of the stylet 20. It is to be noted that the connection point 94 is proximally arranged relative to the cranked portion 88 but distally arranged relative to the cutaway portion 90. The tubular actuator 92 has a slotted bend-enhancing region 96 that lies coincident with the cutaway portion 90 of the outer tubular member 82 of the stylet 20. Relative movement between the outer tubular member 82 and the inner tubular actuator 92 causes deflection of the loop shape 26 in the direction of arrows 98 (FIG. 13).

A size-adjusting actuator in the form of a pull wire 100 is received through lumens of the outer tubular member 82 and the tubular actuator 92 and a distal end of the pull wire 100 is fast with the distal end 86 of the outer tubular member 82. It is to be noted that there is a second longitudinally extending cutaway portion 102 formed between the distal end 86 of the outer tubular member 82 and the cranked region 88 of the outer tubular member 82. This cutaway portion 102 facilitates adjustment of the size of the loop shape 26 by relative movement between the pull wire 100 and the outer tubular member 82.

As shown in FIG. 9, a proximal end of the pull wire 100 is mounted to a stylet carrier in the form of a slide 104 via a suitable mounting formation 105. The mounting formation 105 may include a slot 107 on the slide 104 (shown in FIG. 11) that is appropriately sized to receive the pull wire 100 or a mounting sleeve attached to the proximal end of the pull wire 100. A proximal end of the outer tubular member 82 carries a mounting sleeve 106 and, similarly, a proximal end of the tubular actuator 92 carries a mounting sleeve 108.

The steering control mechanism 72 comprises an elongate, hollow cylindrical member 110. As in the case of other components of the catheter handle 12, the cylindrical member 110 comprises two parts 112 that, in the illustrated embodiment, are clipped together via complementary clips 114 and receiving formations 116. As in the case of the shell parts 34 of the handle body 32, the parts 112 of the cylindrical member 110 could also be hinged together and clipped or screwed closed.

A raised protuberance in the form of a radially outwardly extending knob 118 is defined at a distal end of the steering control mechanism 72 to be engaged by the thumb of a clinician for facilitating steering of the distal end of the catheter sheath 14 during use.

Referring to FIG. 11, the mounting sleeve 106 of the outer tubular member 82 of the stylet 20 is shown mounted in a seat 120 in one of the parts 112 of the steering control mechanism 72. The other part 112 could contain a corresponding part of the seat 120. A further seat 122 is defined proximally of the seat 120 in the passage 40 of the handle body 32 and the mounting sleeve 108 of the tubular actuator 92 is made fast with the seat 122. It will be appreciated that as the steering control mechanism 72 is moved in the direction of arrows 124 relative to the handle body 12, relative movement between the outer tubular member 82 of the stylet 20 and the inner tubular actuator 92 occurs, resulting in deflection of the distal end of the stylet 20 as shown by the arrows 98 in FIG. 13.

As illustrated in FIG. 11, the proximal part of the pull wire 100 is guided around a semispherical guidepost 126 fixedly arranged in the passage 40 of the handle body 32 and the proximal end of the pull wire 100 is mounted fast at 107 with the slide 104.

In an embodiment, the catheter 10 includes a shape, or size, adjustment mechanism 128 (FIGS. 1 and 2). The size adjustment mechanism 128 includes a size adjuster in the form of a collar 130 (FIGS. 1 and 2) arranged on the exterior of the handle body 32 of the catheter handle 12.

The stylet carrier 104 forms part of the size adjustment mechanism 128 and is axially slidably arranged within the passage 40 of the handle body 32 of the catheter handle 12. The collar 130 is, as with other parts of the catheter handle 12, made up of two parts 132 that clip together via complementary clips 134 and receiving formations 136 (FIG. 8). In another embodiment, as illustrated in FIG. 14, the parts 132 of the collar 130 are hinged together with a wing 138 of the hinge shown in FIG. 14. The other side of each part 132 clips together via the clips 134 and receiving formations 136.

As shown more clearly in FIG. 8, the shell parts 34 of the handle body 32 of the catheter handle have a waisted region to define a recess 140 (FIG. 8). The collar 130 is received in the recess 140 and is constrained against axial motion but is free to rotate about a longitudinal axis of the handle body 32.

The recessed region 140 of each shell part 34 further has a cutaway portion 142 defined therein so that when the shell parts 34 are mated together, a longitudinally extending slot is defined in the handle body 32.

Figure 10:
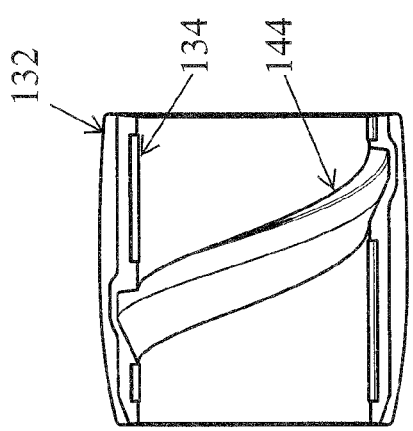
FIG. 10 shows a plan view of a part of a shape adjustment mechanism of the catheter.

The size-adjusting mechanism 128 of the catheter 10 includes complementary guide formations in the form of a camming groove 144 (shown most clearly in FIG. 10) on an internal surface of each part 132 of the collar 130. A complementary guide follower in the form of a pin 146 (FIG. 9) is arranged at that end of the slide 104 opposite the end to which the pull wire 100 is connected. The pin 146 protrudes through the slot in the handle body 32 formed by the cutaway portions 142 of the shell parts 34 and is received in the camming groove 144 of the collar 130. Rotation of the collar 130, therefore, translates into axial displacement of the slide 140. This axial displacement of the slide 140 results in relative movement between the pull wire 100 and the outer tubular member 82 of the stylet 20, resulting in an increase or decrease in the size of the loop shape 26 at the distal part 24 of the stylet 20.

Thus, by rotation of the collar 130 during use, a clinician can control the size of the loop shape 26. This is a simple, one-handed operation. It will be appreciated that the size adjustment mechanism 128 could, in addition or instead, operate as a second steering or deflection mechanism.

It is possible to adjust the effort required to displace the steering control mechanism 72 relative to the handle body 32. For this purpose, a frictional element 150 is provided. The frictional element 150 includes a screw 152 and washer assembly 154, the screw 152 being received in a threaded socket 156 in the shell part 34 of the handle body 32, as shown in FIG. 8. The screw 152 protrudes through a slot 158 defined in a proximal extension limb 160 of one of the parts 112 of the cylindrical member 110 of the steering control mechanism 72.

The catheter 10 includes a connector 162 arranged at the proximal end 36 of the handle body 32 of the catheter handle 12. The connector 162 has terminals 164 to which conductors (not shown) of the electrode 16 of the catheter sheath 14 are connected. The connector 162 sits within the handle body 32 and can be removed and replaced if necessary by separating the shell parts 34. The connector 162 connects to a patient cable of a diagnostic/therapeutic system, with which the catheter 10 is used.

It is a particular advantage of the described embodiments that a compact catheter handle is provided, which lends itself to one-handed use by a clinician. The handle 12 fits easily within the hand of the clinician and all the operating controls such as the steering control mechanism 72 and the size adjustment mechanism 128 fall readily to hand. The steering control mechanism 72 and the size adjustment mechanism 128 are able to be manipulated one-handed by the clinician, which clinicians prefer to do. This enables them to more easily concentrate on positioning and operating the catheter 10.

In addition, catheters are becoming increasingly expensive. Due to their use in potentially biologically hazardous environments, most catheters are used once and then disposed of. Often times, this is unnecessary and the catheters can be re-processed. With the provision of a modular type of handle 10, as described above, it is an easy process to access the interior of the handle 10 to facilitate replacement or refurbishing of the various components and, more particularly, the catheter sheath 14 and the stylet 20, or the connector 162. The handle 12 is a molding of a plastics material and is generally low cost. Thus, should the handle 12 be contaminated with bodily fluids and cannot be adequately cleaned, it is a relatively inexpensive process to dispose of the handle 12 and to replace it with a new one. Even so, because the handle 12 is made up of modular parts, if necessary, only the contaminated parts need to be replaced.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the appended claims below and the description herein, any one of the terms "comprising," "comprised of" or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising" A and B should not be limited to devices consisting only of elements A and B. Any one of the terms "including" or "which includes" or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the appended claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some, but not other, features included in other embodiments, combinations of features of different embodiments are meant to be within the scope of the invention, and form different embodiments, as would be understood by those skilled in the art. For example, in the appended claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

It will be appreciated by persons skilled in the art that numerous variations and/or modifications may be made to the disclosure as shown in the specific embodiments without departing from the scope of the claims. The present embodiments are, therefore, to be considered in all respects as illustrative and not restrictive.

The claims defining the invention are as follows:

1. A catheter handle, comprising:
   a handle body having a proximal end and a distal end and a passage extending between the proximal end and the distal end, the handle body comprising a plurality of shell parts that can be at least partially separated from each other to access an interior of the handle body;
   a connector mounted at the proximal end of the handle body;
   a strain relief arranged distally of the body, the strain relief and the connector being removably arranged relative to the handle body;
   a catheter sheath projecting distally through the strain relief, the catheter sheath having a distal end and a proximal end; and
   a multi-component stylet having a proximal end mounted in the passage of the handle body, the stylet having a distal part preformed into a non-rectilinear shape, wherein the non-rectilinear shape of the preformed distal part of the stylet is imparted to the catheter sheath, and a distal end of the distal part of the stylet is movable within the distal end of the catheter sheath;
   wherein the catheter sheath is extendable distally over the distal end of the stylet.

2. The catheter handle of claim 1, further comprising a catheter sheath carrier received in the passage of the handle body, the strain relief being mounted on a distal end of the catheter sheath carrier.

3. The catheter handle of claim 2, wherein the catheter sheath carrier is slidably received in the passage of the handle body and is slidably displaceable relative to the handle body between a first, retracted position relative to the handle body and a second, extended position relative to the handle body.

4. The catheter handle of claim 2, wherein the catheter sheath carrier comprises a sleeve defining a bore, a support member for supporting a proximal part of a catheter sheath being received in the bore of the sleeve.

5. The catheter handle of claim 4, wherein the sleeve comprises a plurality of parts that are able to be at least partially separated from each other to enable access to be gained to an interior of the sleeve.

6. The catheter handle of claim 2, wherein the catheter sheath carrier and the catheter handle include complementary guide formations for guiding displacement of the catheter sheath carrier relative to the handle body.

7. The catheter handle of claim 6, wherein the complementary guide formations include a locking arrangement for locking the carrier at least in its first position relative to the handle body.

8. The catheter handle of claim 1, further comprising a steering control mechanism.

9. The catheter handle of claim 8, wherein the steering control mechanism is axially displaceable relative to the handle body for effecting steering of the multi-component stylet of the catheter while in use.

10. The catheter handle of claim 9, further comprising a catheter sheath carrier received in the passage of the handle body, the strain relief being mounted on a distal end of the catheter sheath carrier, and wherein the catheter sheath carrier and the catheter handle include complementary guide formations for guiding displacement of the catheter sheath carrier relative to the handle body, and the steering control mechanism comprises a hollow, cylindrical element in which the catheter sheath carrier is received.

11. The catheter handle of claim 9, further comprising an adjustment device for adjusting the friction of displacement of the steering control mechanism relative to the handle body.

12. The catheter handle of claim 10, wherein the cylindrical element comprises a plurality of parts that can be at least partially separated from each other to facilitate access to an interior of the cylindrical element.

13. The catheter handle of claim 8, wherein the steering control mechanism includes a seat for a component of the multi-component stylet.

14. The catheter handle of claim 1, further comprising a size adjuster for adjusting the size of the predetermined shape at a distal end of the multi-component stylet attached to the handle body while in use.

15. The catheter handle of claim 14, wherein the size adjuster comprises a stylet carrier slidably displaceably arranged in the handle body and a collar mounted on an exterior of the handle body to be rotatable about a longitudinal axis of the handle body.

16. The catheter handle of claim 15, wherein the collar and the stylet carrier have complementary motion conversion formations for converting rotary motion of the collar into a predefined motion of the stylet carrier.

17. The catheter handle of claim 15, wherein the stylet carrier includes a mounting formation for mounting a pull wire of the multi-component stylet.

18. The catheter handle of claim 17, wherein the handle body defines a seat for receiving a tubular member of the multi-component stylet while in use.

19. A catheter, comprising:
a catheter handle comprising:
    a handle body having a proximal end and a distal end and a passage extending between the proximal end and the distal end, the handle body comprising a plurality of shell parts that can be at least partially separated from each other to access an interior of the handle body;
    a connector mounted at the proximal end of the handle body; and
    a strain relief arranged distally of the body, the strain relief and the connector being removably arranged relative to the handle body;
a multi-component stylet having a proximal end mounted in the passage of the handle body, the stylet having a distal part preformed into a non-rectilinear shape; and
a catheter sheath projecting distally through the strain relief, the catheter sheath having a distal end and a proximal end, the catheter sheath defining a lumen in which the stylet is received so that the shape of the preformed distal part of the stylet is imparted to a distal part of the catheter sheath, wherein a distal end of the distal part of the stylet is movable within the distal end of the catheter sheath and the catheter sheath is extendable distally over the distal end of the stylet.

20. The catheter of claim 19, further comprising a catheter sheath carrier received in the passage of the handle body, the strain relief being mounted on a distal end of the catheter sheath carrier.

* * * * *